United States Patent
Hoen et al.

(10) Patent No.: US 10,180,721 B2
(45) Date of Patent: Jan. 15, 2019

(54) FABRIC-BASED DEVICES WITH FORCE SENSING

(71) Applicant: Apple Inc., Cupertino, CA (US)

(72) Inventors: Storrs T. Hoen, Brisbane, CA (US); Daniel D. Sunshine, Sunnyvale, CA (US); Aidan N. Zimmerman, Sunnyvale, CA (US); Daniel A. Podhajny, San Jose, CA (US); Maurice P. May, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 15/940,876

(22) Filed: Mar. 29, 2018

(65) Prior Publication Data

US 2018/0364804 A1   Dec. 20, 2018

Related U.S. Application Data

(60) Provisional application No. 62/519,564, filed on Jun. 14, 2017.

(51) Int. Cl.
*G06F 3/01* (2006.01)
*A61B 5/00* (2006.01)
(Continued)

(52) U.S. Cl.
CPC ............ *G06F 3/014* (2013.01); *A41D 1/005* (2013.01); *A41D 31/02* (2013.01); *A61B 5/6806* (2013.01);
(Continued)

(58) Field of Classification Search
CPC combination set(s) only.
See application file for complete search history.

(56) References Cited

U.S. PATENT DOCUMENTS

| 4,437,138 A | | 3/1984 | Nicol | |
|---|---|---|---|---|
| 5,212,372 A | * | 5/1993 | Quick | G06F 3/014 235/462.44 |

(Continued)

FOREIGN PATENT DOCUMENTS

| GB | 2443208 A | 4/2008 |
|---|---|---|
| WO | 2017031153 A1 | 2/2017 |

OTHER PUBLICATIONS

BodiTrak "Smart Fabrics: For Intelligent and Interactive Products" Vista Medical, PatienTech, Apr. 2013. <www.boditrak.com/pdf/Industrial%20BT%20singles%20SCREEN%204-25-2013.pdf>.

*Primary Examiner* — Lisa Lea Edmonds
(74) *Attorney, Agent, or Firm* — Treyz Law Group, P.C.; G. Victor Treyz

(57) ABSTRACT

A fabric-based item such as a fabric glove may include force sensing circuitry. The force sensing circuitry may include force sensor elements formed from electrodes on a compressible substrate such as an elastomeric polymer substrate. The fabric may include intertwined strands of material including conductive strands. Signals from the force sensing circuitry may be conveyed to control circuitry in the item using the conductive strands. Wireless circuitry in the fabric-based item may be used to convey force sensor information to external equipment. The compressible substrate may have opposing upper and lower surfaces. Electrodes for the force sensor elements may be formed on the upper and lower surfaces. Stiffeners may overlap the electrodes to help decouple adjacent force sensor elements from each other. Integrated circuits can be attached to respective force sensing elements using adhesive.

29 Claims, 17 Drawing Sheets

(51) Int. Cl.

| | | |
|---|---|---|
| *G06F 1/16* | (2006.01) | |
| *G06F 3/045* | (2006.01) | |
| *D03D 1/00* | (2006.01) | |
| *A41D 1/00* | (2018.01) | |
| *A41D 31/02* | (2006.01) | |
| *G06F 3/041* | (2006.01) | |
| *G06F 3/044* | (2006.01) | |
| *G06F 3/0488* | (2013.01) | |
| *D02G 3/44* | (2006.01) | |

(52) U.S. Cl.
CPC ......... *A61B 5/6843* (2013.01); *D03D 1/0082* (2013.01); *D03D 1/0088* (2013.01); *G06F 1/163* (2013.01); *G06F 3/044* (2013.01); *G06F 3/045* (2013.01); *G06F 3/0414* (2013.01); *G06F 3/04883* (2013.01); *D02G 3/441* (2013.01); *D10B 2401/16* (2013.01); *D10B 2401/18* (2013.01); *G06F 2203/04102* (2013.01)

(56) References Cited

U.S. PATENT DOCUMENTS

| | | | |
|---|---|---|---|
| 5,983,727 A | 11/1999 | Wellman et al. | |
| 6,035,274 A * | 3/2000 | Kramer | A61B 5/6806 704/270 |
| 6,360,615 B1 | 3/2002 | Smela | |
| 6,452,479 B1 * | 9/2002 | Sandbach | G06F 3/045 338/101 |
| 6,504,531 B1 * | 1/2003 | Sandbach | G06F 3/045 178/18.05 |
| 6,589,171 B2 | 7/2003 | Keirsbilck | |
| 6,701,296 B1 * | 3/2004 | Kramer | A61B 5/6806 370/545 |
| 6,714,117 B2 * | 3/2004 | Sandbach | G06F 3/045 114/210 |
| 6,826,968 B2 | 12/2004 | Manaresi et al. | |
| 7,595,788 B2 | 9/2009 | Son | |
| 7,862,522 B1 | 1/2011 | Barclay et al. | |
| 8,140,143 B2 * | 3/2012 | Picard | A61B 5/0531 600/388 |
| 8,368,641 B2 | 2/2013 | Tremblay et al. | |
| 8,925,392 B2 * | 1/2015 | Esposito | A61B 5/1036 73/862.01 |
| 9,301,563 B2 * | 4/2016 | Hardy | A41D 19/0031 |
| 9,582,072 B2 * | 2/2017 | Connor | G06F 3/011 |
| 9,830,783 B1 * | 11/2017 | Kessler | G08B 6/00 |
| 2006/0167564 A1 * | 7/2006 | Flaherty | A61B 5/0476 623/57 |
| 2011/0087115 A1 | 4/2011 | Sackner et al. | |
| 2012/0226197 A1 | 9/2012 | Sanders et al. | |
| 2013/0197399 A1 * | 8/2013 | Montgomery | A61B 5/1121 600/595 |
| 2014/0135593 A1 | 5/2014 | Jayalth et al. | |
| 2015/0091859 A1 | 4/2015 | Rosenberg et al. | |
| 2015/0122042 A1 | 5/2015 | Lin et al. | |
| 2015/0370320 A1 * | 12/2015 | Connor | A61B 5/6831 345/173 |
| 2015/0375042 A1 * | 12/2015 | Schaffer | A61B 5/1116 482/8 |
| 2016/0018274 A1 | 1/2016 | Seitz | |
| 2016/0052131 A1 * | 2/2016 | Lessing | B25J 9/142 361/679.01 |
| 2016/0169754 A1 * | 6/2016 | Kowalewski | G01L 5/228 73/862.046 |
| 2016/0327979 A1 | 11/2016 | Lettow | |
| 2016/0338621 A1 * | 11/2016 | Kanchan | A61B 5/0022 |
| 2017/0086519 A1 * | 3/2017 | Vigano' | D02G 3/00 |

\* cited by examiner

US 10,180,721 B2

FABRIC-BASED DEVICES WITH FORCE SENSING

This patent application claims the benefit of provisional patent application No. 62/519,564, filed on Jun. 14, 2017, which is hereby incorporated by reference herein in its entirety.

FIELD

This relates generally to force sensing and, more particularly, to items such as fabric-based items with force sensing capabilities.

BACKGROUND

It may be desirable to form items using materials such as fabric. For example, wearable items may be formed from fabric. Some wearable items may include sensing circuitry. Electronic equipment may use information from the sensing circuitry in controlling a system or performing other tasks.

If care is not taken, fabric-based items such as these may not offer desired features. For example, a fabric-based item with sensing circuitry may be awkward to use, may not have an attractive appearance, or may not gather measurements accurately.

SUMMARY

A fabric-based item such as a fabric glove may include force sensing circuitry. The force sensing circuitry may include force sensor elements formed from electrodes on a compressible substrate such as an elastomeric polymer substrate. The fabric may include intertwined strands of material including conductive strands. Signals from the force sensing circuitry may be conveyed to control circuitry in the item using the conductive strands. Wireless circuitry in the fabric-based item may be used to convey force sensor information to external equipment.

The compressible substrate may have opposing upper and lower surfaces. Electrodes for the force sensor elements may be formed on the upper and lower surfaces. Stiffeners may overlap the electrodes to help decouple adjacent force sensor elements from each other. In some configurations, integrated circuits can be attached to respective force sensing elements using adhesive.

Force sensing elements may have sets of electrodes that are arranged in an array on the compressible substrate such as a one-dimensional array. The compressible substrate may be formed from an elongated strip of the elastomeric polymer and may be sufficiently elongated to serve as a strand that is intertwined with the conductive strands and other intertwined strands of material in the fabric.

To facilitate deformation of the compressible substrate, the compressible substrate may be provided with openings surrounding the electrodes of each force sensor element. Electrodes, signal traces for conveying capacitive force sensor signals, shield structures, and other conductive signal paths in the force sensing circuitry may be formed from structures that resist cracking when flexed such as mesh structures with serpentine line segments.

DETAILED DESCRIPTION

Figure 1:
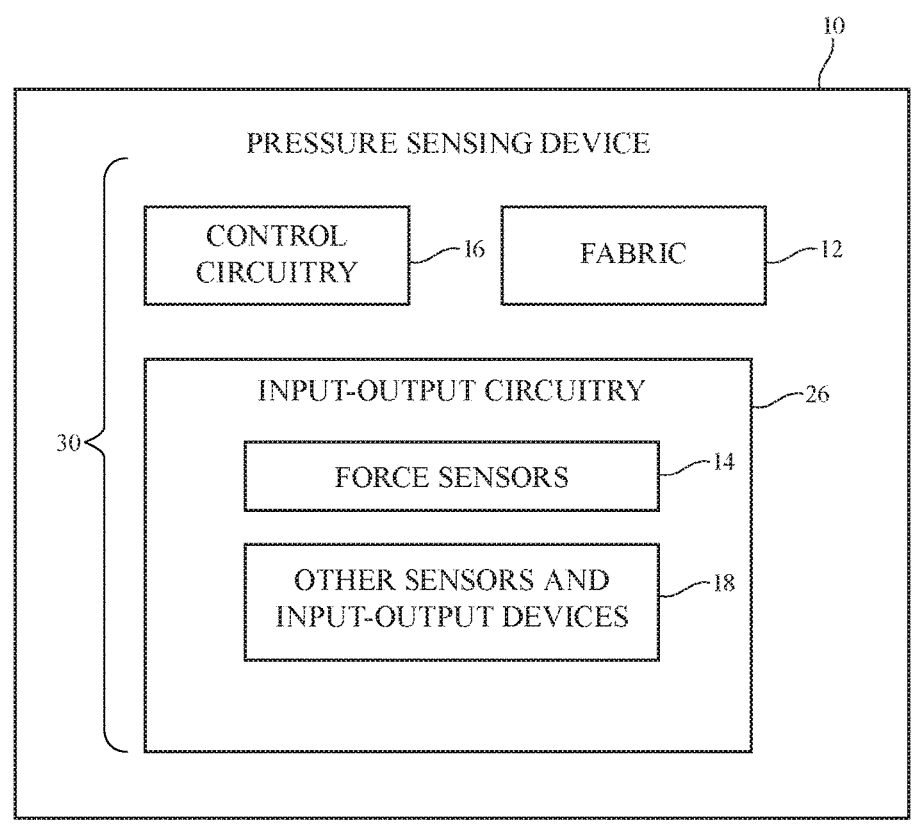
FIG. 1 is a schematic diagram of an illustrative fabric-based item in accordance with an embodiment.

A schematic diagram of an illustrative item that contains force sensors is shown in FIG. 1. Item 10 may be an electronic device or an accessory for an electronic device such as a laptop computer, a computer monitor containing an embedded computer, a tablet computer, a cellular telephone, a media player, or other handheld or portable electronic device, a smaller device such as a wrist-watch device, a pendant device, a headphone or earpiece device, a device embedded in eyeglasses or other equipment worn on a user's head, or other wearable or miniature device, a television, a computer display that does not contain an embedded computer, a gaming device, a remote control, a navigation device, an embedded system such as a system in which item 10 is mounted in a kiosk, in an automobile, airplane, or other vehicle, other electronic equipment, or may be equipment that implements the functionality of two or more of these devices. If desired, item 10 may be a removable external case for electronic equipment, may be a strap, may be a wrist band or head band, may be a removable cover for a device, may be a case or bag that has straps or that has other structures to receive and carry electronic equipment and other items, may be a necklace or arm band, may be a wallet, sleeve, pocket, or other structure into which electronic equipment or other items may be inserted, may be part of a chair, sofa, or other seating (e.g., cushions or other seating structures), may be part of an item of clothing or other wearable item (e.g., a hat, belt, wrist band, headband, sock, glove, shirt, pants, etc.), or may be any other suitable item. Configurations in which item 10 is a glove or other wearable item may sometimes be described herein as an example. This is, however, merely illustrative. Item 10 may be any suitable device.

Item 10 may include intertwined strands of material that form fabric 12, so items such as item 10 may sometimes be referred to as fabric-based items or fabric-based electronic devices. Fabric 12 may form all or part of a housing wall or other layer in an electronic device (e.g., when item 10 is a glove or other flexible device worn by a user), may form an outer covering for a housing wall structure, may form internal structures in an electronic device, or may form other fabric-based structures. Item 10 may be soft (e.g., item 10 may have a fabric surface that yields to a light touch), may have a rigid feel (e.g., the surface of item 10 may be formed from a stiff fabric), may be coarse, may be smooth, may have ribs or other patterned textures, and/or may be formed as part of a device that has portions formed from non-fabric structures of plastic, metal, glass, crystalline materials, ceramics, or other materials.

The strands of material in fabric 12 may be single-filament strands (sometimes referred to as fibers or monofilaments), may be yarns or other strands that have been formed by intertwining multiple filaments (multiple monofilaments) of material together, or may be other types of strands (e.g., tubing). Monofilaments for fabric 12 may include polymer monofilaments and/or other insulating monofilaments and/or may include bare wires and/or insulated wires. Monofilaments formed from polymer cores with metal coatings and monofilaments formed from three or more layers (cores, intermediate layers, and one or more outer layers each of which may be insulating and/or conductive) may also be used.

Yarns in fabric 12 may be formed from polymer, metal, glass, graphite, ceramic, natural materials as cotton or bamboo, or other organic and/or inorganic materials and combinations of these materials. Conductive coatings such as metal coatings may be formed on non-conductive material. For example, plastic yarns and monofilaments in fabric 12 may be coated with metal to make them conductive. Reflective coatings such as metal coatings may be applied to make yarns and monofilaments reflective. Yarns may be formed from a bundle of bare metal wires or metal wire intertwined with insulating monofilaments (as examples).

Strands of material may be intertwined to form fabric 12 using intertwining equipment such as weaving equipment, knitting equipment, or braiding equipment. Intertwined strands may, for example, form woven fabric, knit fabric, braided fabric, etc. Conductive strands and insulating strands may be woven, knit, braided, or otherwise intertwined to form contact pads that can be electrically coupled to conductive structures in item 10 such as the contact pads of an electrical component. The contacts of an electrical component may also be directly coupled to an exposed metal segment along the length of a conductive yarn or monofilament.

Conductive and insulating strands may also be woven, knit, or otherwise intertwined to form conductive paths. The conductive paths may be used in forming signal paths (e.g., signal buses, power lines, etc.), may be used in forming part of a capacitive touch sensor electrode, a resistive touch sensor electrode, a force sensor electrode, or other input-output device, or may be used in forming other patterned conductive structures. Conductive structures in fabric 12 may be used in carrying power signals, digital signals, analog signals, sensor signals, control signals, data, input signals, output signals, or other suitable electrical signals.

Item 10 may include mechanical structures in addition to fabric 12 such as polymer binder to hold strands in fabric 12 together, support structures such as frame members, housing structures (e.g., an electronic device housing), and other mechanical structures.

Item 10 may include circuitry 30. Circuitry 30 may include electrical components that are coupled to fabric 12, electrical components that are housed within an enclosure formed by fabric 12 and/or an enclosure formed using other housing structures such as housing walls formed from plastic, metal, glass, ceramic, or other materials, electrical components that are attached to fabric 12 using welds, solder joints, adhesive bonds (e.g., conductive adhesive bonds such as anisotropic conductive adhesive bonds or other conductive adhesive bonds), crimped connections, or other electrical and/or mechanical bonds. Circuitry 30 may include metal structures for carrying current, electrical components such as integrated circuits, discrete components (e.g., capacitors, resistors, and inductors), and/or other circuitry.

As shown in FIG. 1, circuitry 30 may include input-output circuitry 26 and control circuitry 16. Input-output circuitry 26 may include force sensors 14 (sometimes referred to as pressure sensors) and other sensors and input-output devices 18. Devices 18 may include light-emitting diodes, displays, speakers, microphones, buttons, tone generators, haptic output devices such as vibrators, and sensors (e.g., gas sensors, gas pressure sensors, temperature sensors, strain gauges, accelerometers, proximity sensors, touch sensors, ambient light sensors, digital image sensors, fingerprint sensors, gaze detection and eye and face sensing devices, and/or other sensors).

Control circuitry 16 may be formed from one or more integrated circuits such as microprocessors, microcontrollers, application-specific integrated circuits, digital signal processors, and/or other circuits. Control circuitry 16 may be used to gather information from user input circuitry, sensing circuitry such as touch sensors, proximity sensors, and other sensing circuitry, and other input-output devices 18 and may be used in gathering and processing force sensor information from force sensors 14. Control circuitry 16 may be used to control the operation of item 10 based on this gathered information and/or based on other information by controlling electrically controllable (electrically adjustable) components in circuitry 16. The control circuitry may have wireless communications circuitry and other communications circuitry and may be used in supporting communications with external equipment. Using wireless communications or wired communications, control circuitry in item 10 may, if desired, provide information such as force sensor information and/or other information gathered using input-output devices 18 to external equipment.

External equipment that communicates with item 10 may include separate items that are configured to operate with each other. For example, item 10 may be a case that operates with a device that fits within the case. As another example, item 10 may be a force sensing glove or other wearable device and may be used in controlling an electronic device that is using information such as force sensor measurements from force sensors in item 10. Devices that may be controlled using force sensor information from a force sensing glove or other item 10 include a gaming unit, a computer, a set-top box, a television, and or other electronic equipment.

To supply force sensor measurements (e.g., raw measurements or commands or other information derived from raw measurements) to external equipment, circuitry 16 may include wireless communications circuitry such as antennas, wireless radio-frequency transceivers (e.g., transceivers operating at 2.4 GHz, 5 GHz, and/or other wireless communications frequencies) and other electrical components for supporting wireless communications with external electronic devices. If desired, the wireless communications circuitry may be based on infrared transmitters such as infrared light-emitting diodes or lasers for transmitting infrared commands to electronic equipment.

Fabric 12 may be used in forming a force sensing glove or other electronic device. The fabric may serve as a supporting structure for the body of the glove or other device or, in some configurations, may serve as an inner liner, outer covering, or other portion of a supporting structure that also includes other structural components. Fabric 12 may be formed from strands that are intertwined using any suitable intertwining equipment. With one suitable arrangement, which may sometimes be described herein as an example, fabric 12 may be woven fabric formed using a weaving machine. In this type of illustrative configuration, fabric 12 may have a plain weave, a basket weave, a satin weave, a twill weave, or variations of these weaves, may be a three-dimensional woven fabric, or may be other suitable fabric. With other suitable arrangements, fabric 12 may be knit or braided. If desired, signal paths formed from conductive yarns and monofilaments (e.g., insulated and bare wires) may be used to route signals within item 10 and may be used to route signals between item 10 and external devices.

Figure 2:
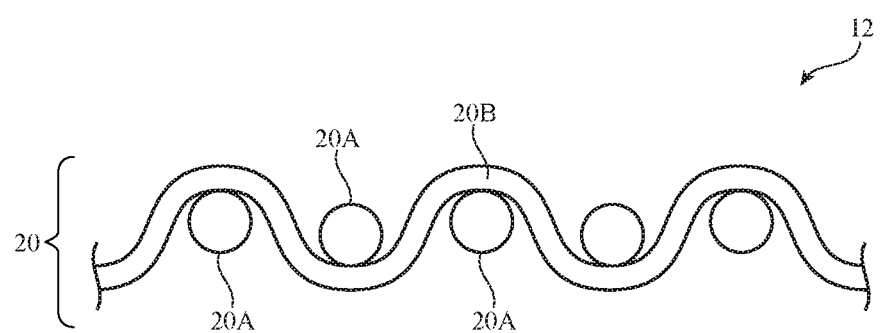
FIG. 2 is a side view of illustrative woven fabric in accordance with an embodiment.

A cross-sectional side view of illustrative woven fabric 12 is shown in FIG. 2. As shown in FIG. 2, fabric 12 may include strands 20 such as warp strands 20A and weft strands 20B. In the illustrative configuration of FIG. 2, fabric 12 has a single layer of woven strands 20. Multi-layer fabric constructions may be used for fabric 12 if desired.

Figure 3:
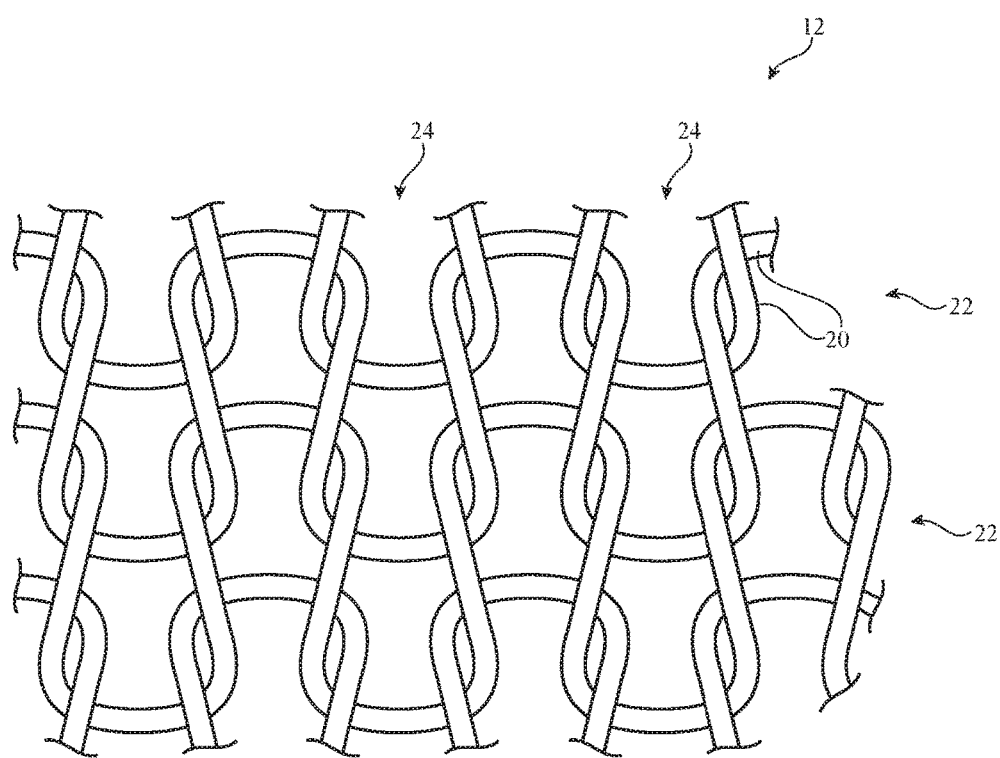
FIG. 3 is a top view of illustrative knit fabric in accordance with an embodiment.

As shown in FIG. 3, fabric 12 may be a knit fabric. In the illustrative configuration of FIG. 3, fabric 12 has a single layer of knit strands 20 that form horizontally extending rows of interlocking loops (courses 22) and vertically extending wales 24. Other types of knit fabric may be used in item 10, if desired.

Item 10 may include non-fabric materials (e.g., structures that are formed from plastic, metal, glass, ceramic, crystalline materials such as sapphire, leather, etc.). These materials may be formed using molding operations, extrusion, machining, laser processing, and other fabrication techniques and may be used in forming housing structures, internal mounting structures, buttons, portions of display components and other electronic components, and/or other structures in item 10. In some configurations, item 10 may include one or more layers of material. The layers in item 10 may include layers of polymer, metal, glass, fabric, leather, adhesive, crystalline materials, ceramic, substrates on which components have been mounted, patterned layers of material, layers of material containing patterned metal traces, thin-film devices such as transistors, and/or other layers.

Figure 4:
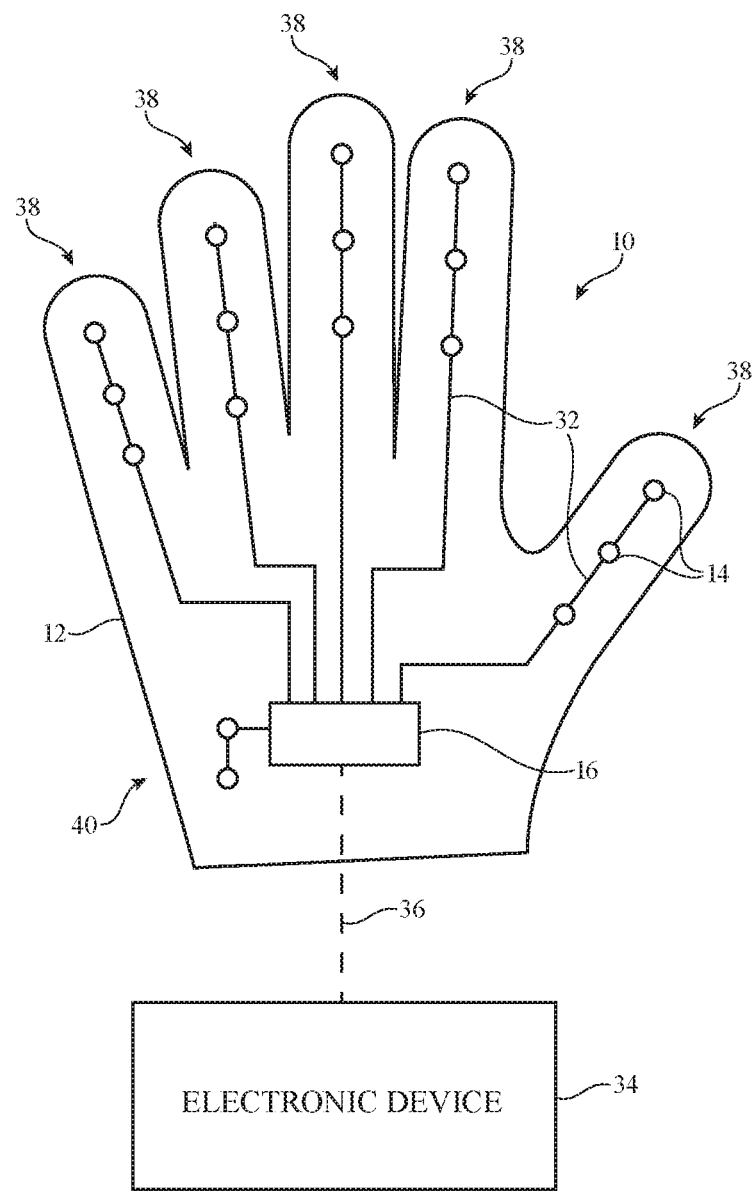
FIG. 4 is a diagram of an illustrative fabric-based item such as a glove with sensor circuitry coupled to an electronic device in accordance with an embodiment.

As shown in FIG. 4, item 10 may include a layer of fabric 12 and/or other layers of material shaped in the form of a glove. Force sensing circuitry such as force sensors 14 may be located on one or more fingers 38 of the glove (e.g., on the top, bottom, and/or sides of fingers 38) and/or on other areas of the glove such as on palm 40 or the top surface of the glove that covers the back of a user's hand. Signal paths 32 may be used in electrically coupling force sensors 14 to control circuitry 16. Signal paths 32 may be formed from conductive strands 20 in fabric 12 and/or separate conductive strands (wires, traces on printed circuits, etc.). Control circuitry 16 may have wired or wireless communications circuitry for supporting communications over communications link 36 between item 10 and external electronic devices such as electronic device 34. Device 34 may be a computer, cellular telephone, a head-mounted device, a display, a gaming unit, a set-top box, a system including two or more of these devices, or other electronic equipment. During operation, control circuitry 16 may use force sensors 14 to gather force sensor measurements and may, as an example, provide this information to electronic device 34 for controlling device 34. If desired, control circuitry in external equipment 34 may be used in processing sensor data (e.g., to minimize the amount of circuitry in item 10). Force sensor measurements may be used in a glove or other input device, in clothes, as part of a heart rate sensor, blood pressure sensor, respiration sensor, etc.

Figure 5:
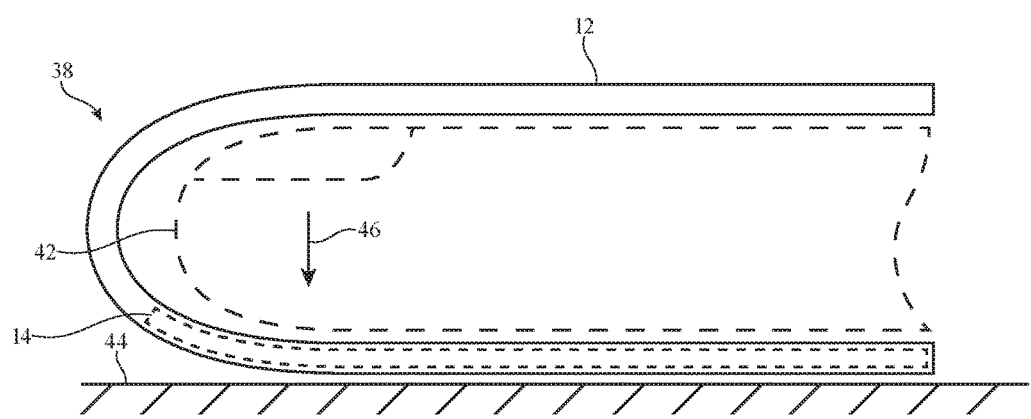
FIG. 5 is a cross-sectional side view of an illustrative glove finger with sensor circuitry such as force sensors in accordance with an embodiment.

FIG. 5 is a cross-sectional side view of an illustrative portion of item 10 (e.g., a glove) such as a finger portion. As shown in FIG. 5, glove finger 38 may include fabric 12 that has been woven, knit, braided and/or sewn to form a shape appropriate for receiving a user's finger (e.g., finger 42). When the user presses glove finger 38 in direction 46 towards surface 44 with finger 42, a compressive force will be applied to fabric 12 and force sensors 14 between finger 42 and surface 44. Surface 44 may be an external surface such as a table top or may be an inner surface of a glove-shaped outer shell (housing) against which the user may press. Control circuitry 16 (FIG. 4) can measure this force using force sensors 14.

Figure 6:
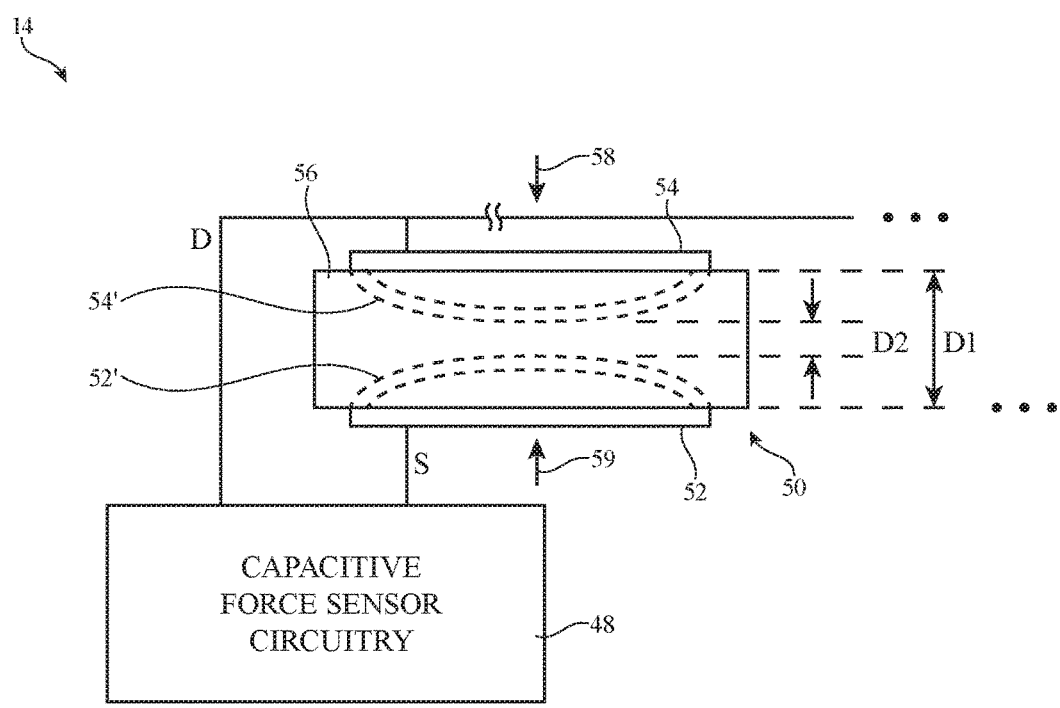
FIG. 6 is a cross-sectional side view of an illustrative capacitive force sensor in accordance with an embodiment.

An illustrative force sensor is shown in FIG. 6. Force sensor 14 may include capacitive force sensor processing circuitry such as circuitry 48 and a capacitive force sensor element such as force sensor element 50. Capacitive force sensor circuitry 48 may be implemented using one or more integrated circuits and may be used to apply alternating current signals to elements such as element 50 (e.g., drive signals D) while monitoring resulting signals (sense signals S). By processing the D and S signals, circuitry 48 can measure the capacitance of element 50 and can detect any changes to this capacitance due to applied force. Any suitable capacitance sensing techniques may be used in processing capacitance measurements (e.g., mutual capacitance or self capacitance).

Element 50 may include capacitive force sensing electrodes 52 and 54. Conductive strands in fabric 12 and/or other signal paths may be used in electrically coupling capacitive force sensor circuitry 48 to electrodes 52 and 54. Electrodes 52 and 54 may be separated by substrate 56. Substrate 56 may be formed from an elastomeric polymer such as silicone or other compressible material. Elastomeric polymer substrate 56 may be insulating. When no force is applied to element 50, electrodes 52 and 54 will be separated by a distance D1. When force is applied to element 50 in directions 58 and 59, elastomeric polymer substrate 56 will deform inwardly and the distance between electrodes 52 and 54 will decrease to distance D2. This will cause the capacitance between electrodes 52 and 54 to rise, which can be detected by capacitive force sensor circuitry 48.

Figure 7:
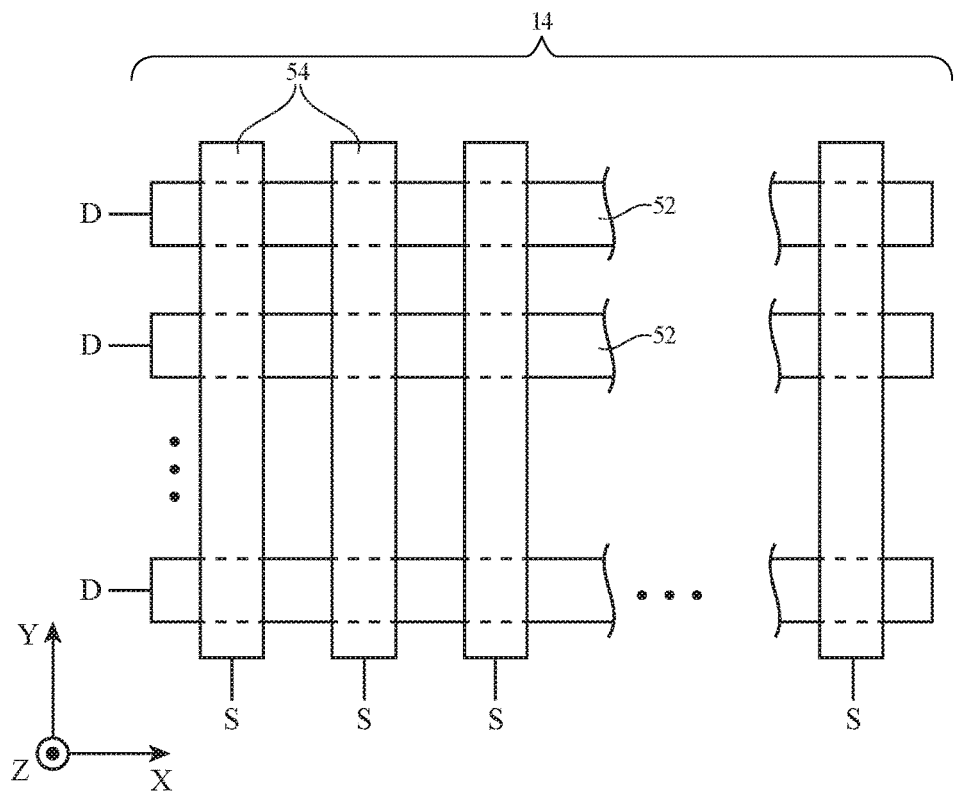
FIGS. 7 and 8 are diagrams of illustrative arrays of electrodes for capacitive force sensors in accordance with an embodiment.
Figure 8:
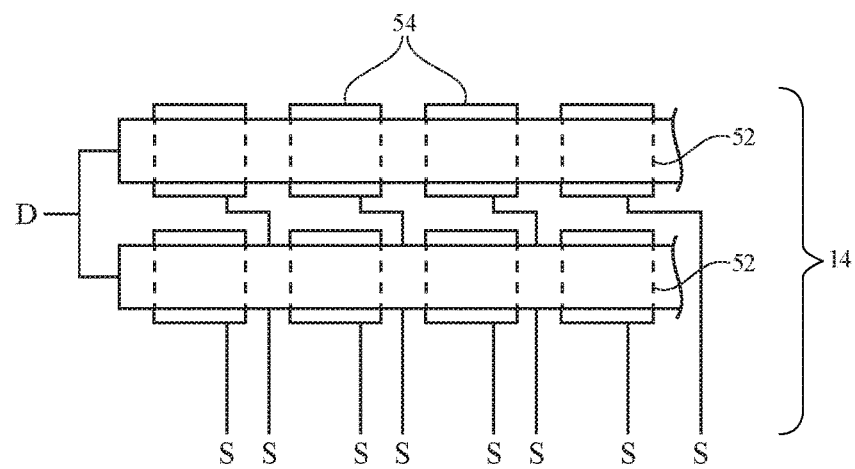

There may be any suitable number of elements 50 and any suitable number of integrated circuits for implementing circuitry 48 in item 10. FIG. 7 is a diagram of an illustrative force sensor formed from multiple vertical strip-shaped electrodes 52 that carry drive signal D and multiple horizontal strip-shaped electrodes 54 that provide sense signals S to circuitry 48. Electrodes 52 and 54 may run perpendicular to each other and may be formed form metal traces on opposing sides of an elastomeric layer such as elastomeric polymer substrate 56 of FIG. 6. The electrode pattern of FIG. 7 allows two-dimensional force measurements (in dimensions X and Y) to be gathered by circuitry 16. In the illustrative configuration of FIG. 8, drive electrodes 52 receive a common drive signal D and each sense electrode 54 is coupled to an independent sense signal line for providing a respective independent sense signal to circuitry 48. In configurations such as these, each intersection between drive and sense electrodes serves as a separate element 50. Electrodes 52 and 54 of FIGS. 7 and 8 may be separated by a compressible material such as an elastomeric material (e.g., substrate 56). If desired, other electrode patterns may be used in forming force sensor 14. The configurations of FIGS. 7 and 8 are merely illustrative.

Figure 9:
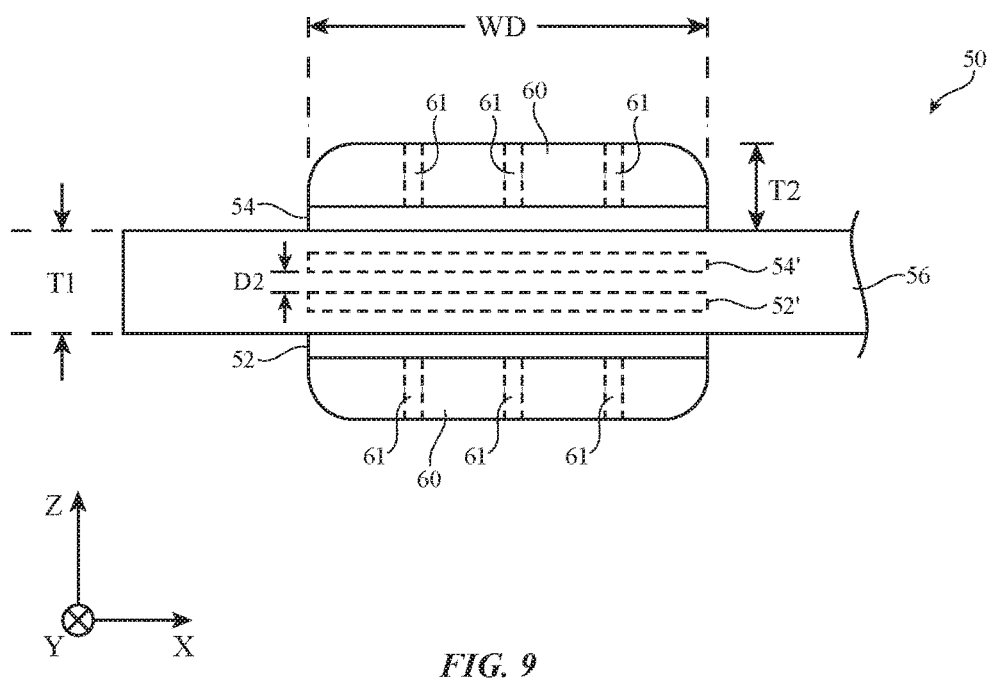
FIG. 9 is a cross-sectional side view of an illustrative capacitive force sensor in accordance with an embodiment.

FIG. 9 is a cross-sectional side view of an illustrative capacitive force sensor element. As shown in FIG. 9, element 50 may have a compressible layer such as elastomeric polymer substrate 56 that separates electrodes 52 and 54 as described in connection with FIG. 6. When polymer substrate 56 is compressed, the separation distance T1 between electrodes 52 and 54 decreases to a distance D2 that is less than distance T1 as illustrated by compressed electrode positions 52' and 54'. This changes the capacitance between electrodes 52 and 54, which can be measured and used in determining how much force has been applied to element 50.

Optional stiffeners 60 may be formed on top of electrodes 52 and 54 to help decouple sensor element 50 from adjacent sensor elements 50 (e.g., to help reduce cross-talk). If desired, there may be multiple stiffener structures over each pair of electrodes (e.g., stiffener 60 of FIG. 9 may be segmented by forming gaps 61 that divide stiffeners 60 to form smaller stiffener segments). In some arrangements, only one stiffener 60 is used (e.g., lower stiffener structures may be omitted from electrode 52 so that only the stiffener structure on electrode 54 is present).

The thickness T1 of the layer of elastomeric polymer substrate 56 in element 50 may be, for example, 20-100 microns, at least 3 microns, at least 15 microns, at least 40 microns, less than 400 microns, less than 200 microns, or other suitable thickness. The thickness T2 of stiffeners 60 may be, for example, 50-300 microns, at least 10 microns, at least 25 microns, less than 1000 microns, less than 500 microns, or other suitable thickness. Stiffeners 60 may be formed form a polymer, metal, or other material that is more rigid than elastomeric polymer substrate 56. For example, elastomeric polymer substrate 56 may be formed from an elastomeric polymer characterized by a first modulus of elasticity (e.g., a Young's modulus or other elastic modulus) and stiffeners 60 may be characterized by a second modulus of elasticity that is greater than the first modulus of elasticity. The Young's modulus of elasticity of polymer substrate 56 may be 0.1 MPa to 10 MPa, greater than 0.2 MPa, less than 5 MPa, etc. The Young's modulus of elasticity of stiffeners 60 may be 100 MPa to 200 GPa, more than 150 MPa, less than 150 GPa, etc. The thickness of electrodes 52 and 54 may be less than 20 microns, less than 10 microns, less than 3 microns, less than 0.5 microns, more than 0.01 microns, more than 0.2 microns, or other suitable thickness. Electrodes 52 and 54 may be formed from metal traces (e.g., metal traces deposited using physical vapor deposition, electroplating, etc.) and/or may be formed form patterned conductive structures such as patterned metal ink (e.g., printed silver paint or other metal paint, graphene, graphite, silver particles, or other conductive material in a polymer such as silicone, PEDOT:PSS or poly(3,4-ethylenedioxythiophene) polystyrene sulfonate conductive polymer, etc.). The width WD of stiffeners 60 and electrodes 54 and 52 (e.g., the diameter or other lateral dimension in the XY plane of FIG. 9) may be 2-3 mm, at least 0.1 mm, at least 0.5 mm, at least 1 mm, less than 10 mm, less than 4 mm, or other suitable dimension. Stiffeners 60 help translate applied pressure on the surface of stiffeners 60 into compression of the elastomeric material directly between the stiffeners, thereby helping to avoid undesired coupling between adjacent elements 50 that could reduce measurement accuracy. The use of locally stiff areas (e.g., stiffeners 60) and the use of a flexible substrate that allows individual sensors to be compressed without crosstalk helps to accommodate variations in fabric morphology and finger curvature while minimizing longitudinal substrate stress.

Figure 10:
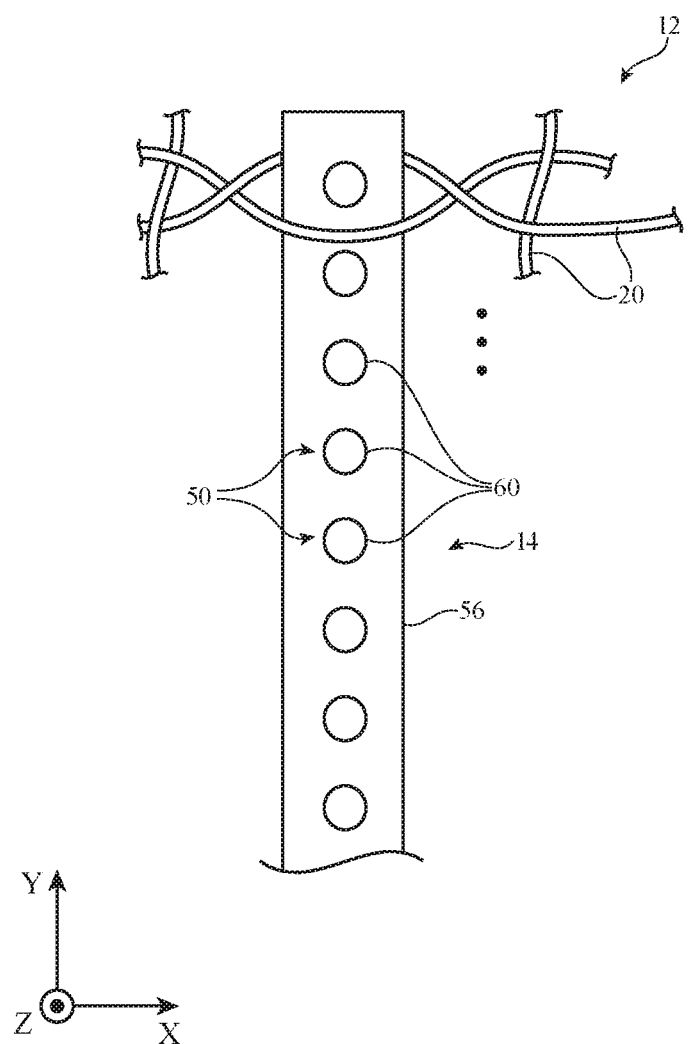
FIG. 10 is a top view of an illustrative strip-shaped substrate and associated array of force sensor elements incorporated into fabric in accordance with an embodiment.

To facilitate incorporation of force sensor 14 into fabric 12, sensor elements 50 may be formed on an elongated strip-shaped flexible substrate such as elastomeric polymer substrate 56 of FIG. 10. The aspect ratio of substrate 56 (length over width) may be at least 10, at least 25, at least 100, less than 1000, or other suitable aspect ratio. Sensor elements 50 may, in general, be arranged in a two-dimensional array (e.g., extending across both the X and Y dimensions when sensor 14 lies in an XY plane) or a one-dimensional array. Sensor 14 of FIG. 10 has a one-dimensional array configuration in which substrate 56 is elongated along the Y axis and in which sensor elements 50 are arranged in a single row extending along the Y axis. If desired, narrow strip-shaped sensors can be formed using multiple closely spaced rows of elements 56 (e.g., a 2×N arrangement in which N is the number of elements 50 that extend along the longitudinal axis of the sensor substrate). The use of a narrow sensor substrate arrangement with a single one-dimensional array of elements 50 and/or a relatively narrow two-dimensional array of elements 50 allows sensor 14 to form a strand of material that can be incorporated into fabric 12 amongst other strands 20 as shown in FIG. 10. Strands formed from elongated compressible substrates and narrow arrays of force sensor elements 50 may serve as warp strands or weft strands in woven fabric or may be incorporated into knit or braided fabric.

Figure 11:
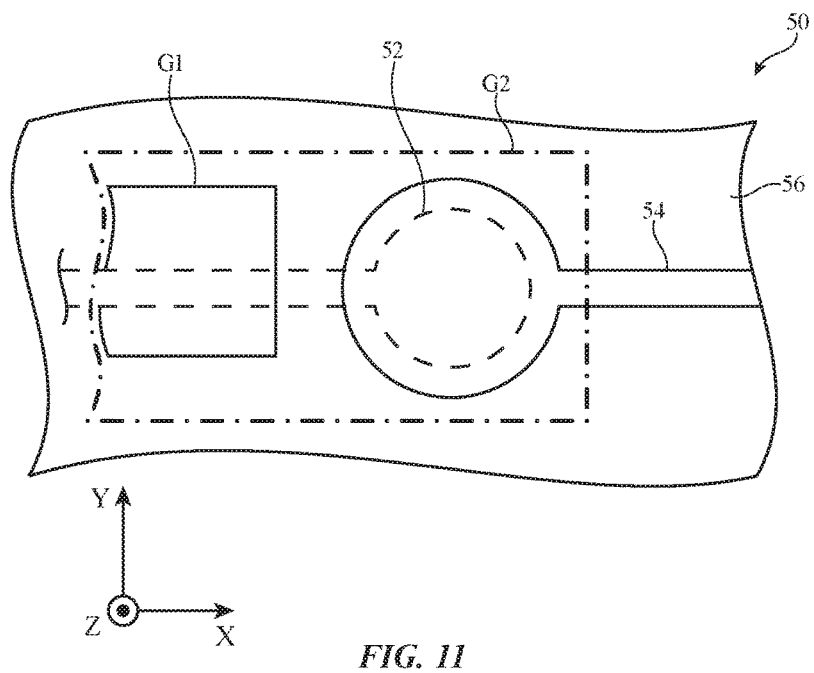
FIG. 11 is a top view of an illustrative force sensor in accordance with an embodiment.
Figure 12:
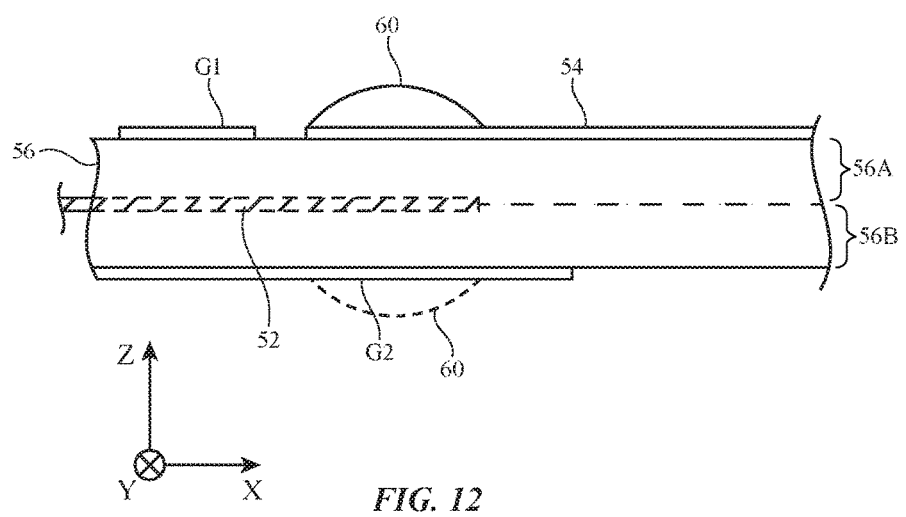
FIG. 12 is a cross-sectional side view of the force sensor of FIG. 11 in accordance with an embodiment.

If desired, electrical shielding structures may be incorporated into sensors 14. For example, grounded conductive layers may be formed above and/or below sensor signal paths. This type of arrangement is shown in the top view of sensor element 50 in FIG. 11 and the corresponding side view of FIG. 12. As shown in FIGS. 11 and 12, sensor element 50 may include electrodes 54 and 52 that are located on opposing surfaces of an substrate 56 Grounded shielding structures such as shield layer G2 and shield layer G1 may help shield signal paths in element 50. For example, shield G1 may be formed on the upper surface of substrate 56 and shield G2 may be formed on the opposing lower surface of substrate 56 so that these shield layers overlap portions of electrodes 52 and 54. Substrate 56 may be formed from multiple elastomeric layers such as layer 56A and 56B. Layers 56A and 56B may be coupled together (e.g., using a layer of adhesive). Electrode 52 may be formed between layers 56A and 56B (as an example). Optional stiffeners 60 may be formed on both electrode 54 and the opposing side of substrate 56 (e.g., on shield G2 where shield G2 overlaps electrode 54) and/or one or both of these stiffeners may be omitted. If desired, shields can be formed around drive electrode 54. In some configurations, conductive strands in fabric can form shields.

Figure 13:
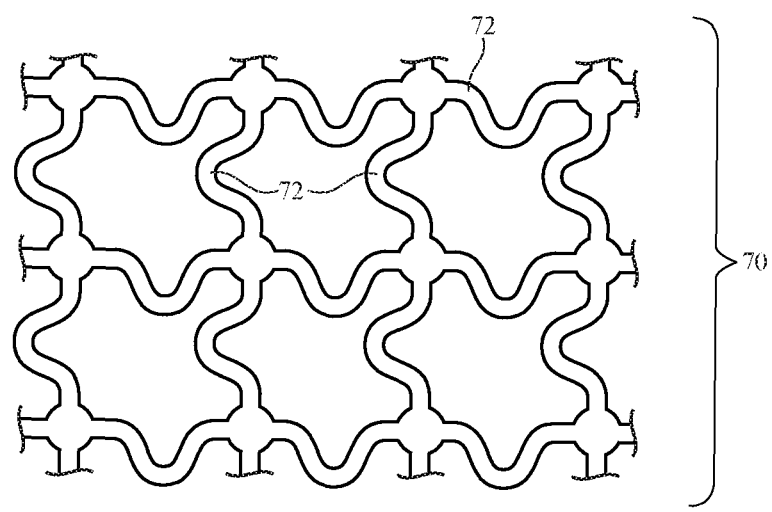
FIG. 13 is a diagram of an illustrative conductive mesh structure of the type that may be used in forming conductive paths in force sensor circuitry in accordance with an embodiment.

To prevent cracks from forming in the conductive layers of sensor 14, one or more of these conductive layers may be formed using serpentine lines. As an example, one or more conductors in sensor 14 such as electrodes 52 and 54 and shielding layers G1 and G2 may be formed using a mesh of serpentine lines (see, e.g., serpentine lines 72 of mesh 70 in the example of FIG. 13). Isolated (non-mesh-shaped) paths formed from serpentine lines may also be used (e.g., to convey signals between force sensor elements 50 and force sensor processing circuitry). Lines 72 may be formed from metal traces deposited and patterned on substrate 56 using photolithography and/or may be metal layers formed from metal paint or other conductive materials.

Figure 14:
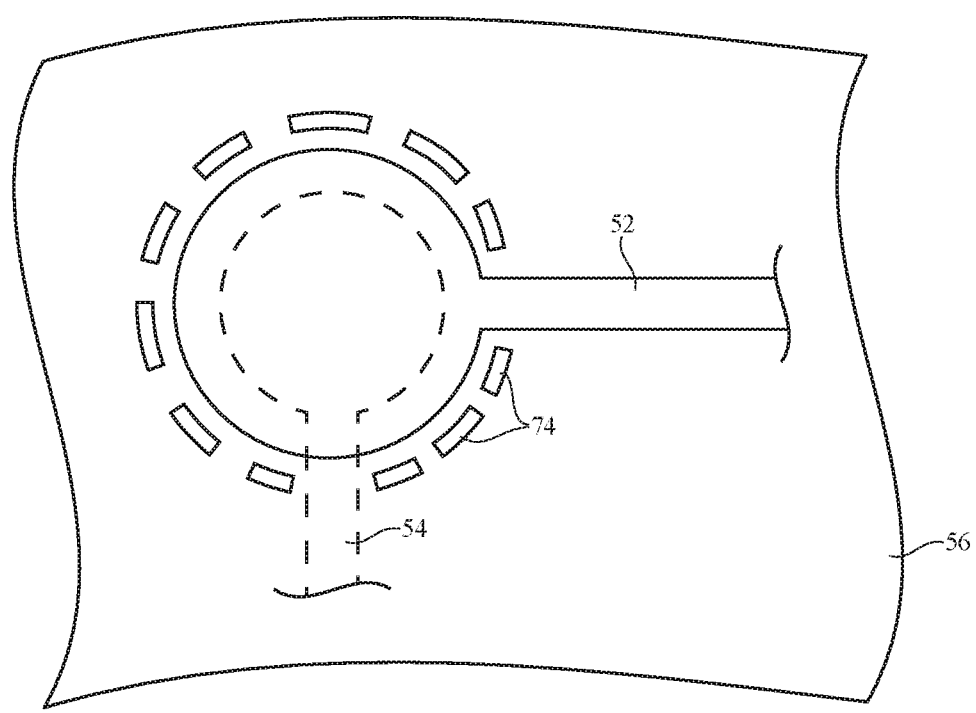
FIG. 14 is a top view of an illustrative force sensor formed from metal traces on an elastomeric layer having through-holes or other openings to facilitate deformation of the elastomeric layer in accordance with an embodiment.

To enhance the flexibility of substrate 56, one or more areas of substrate 56 may be provided with openings. The openings may be recesses that pass partially through substrate 56 and/or may be through holes that pass between opposing surfaces of substrate 56. Flexibility-enhancement structures such as these may, if desired, be concentrated around electrodes 52 and 54 to facilitate compression of the portion of substrate 56 that overlaps electrodes 52 and 54. As shown in FIG. 14, for example, openings 74 that pass partly or entirely through substrate 56 may be arranged in a ring-shaped pattern such as a circular ring surrounding electrodes 52 and 54. This may facilitate compression of the portion of substrate 56 that is interposed between electrodes 52 and 54 when a user compresses force sensing element 50 during use of item 10.

Figure 15:
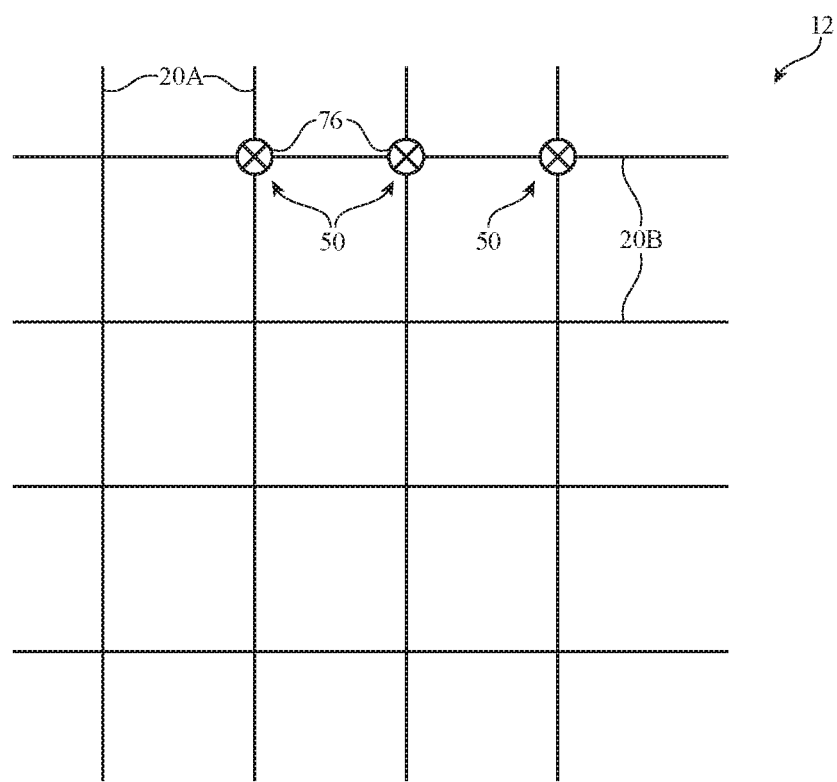
FIG. 15 is a top view of illustrative fabric having an array of force sensors in accordance with an embodiment.

In the arrangement of FIG. 15, fabric 12 includes woven strands such as warp strands 20A and weft strands 20B. Force sensing elements 50 may be formed at intersections 76 of strands 20A and 20B (e.g., at the intersections of conductive strands among strands 20A and 20B) and may be electrically coupled to these strands. This allows signals for the force sensor elements to be routed through the conductive strands of fabric 12. Signals can also be routed through signal paths (wires, flexible printed circuits, etc.) that are separate from fabric 12, if desired.

Figure 16:
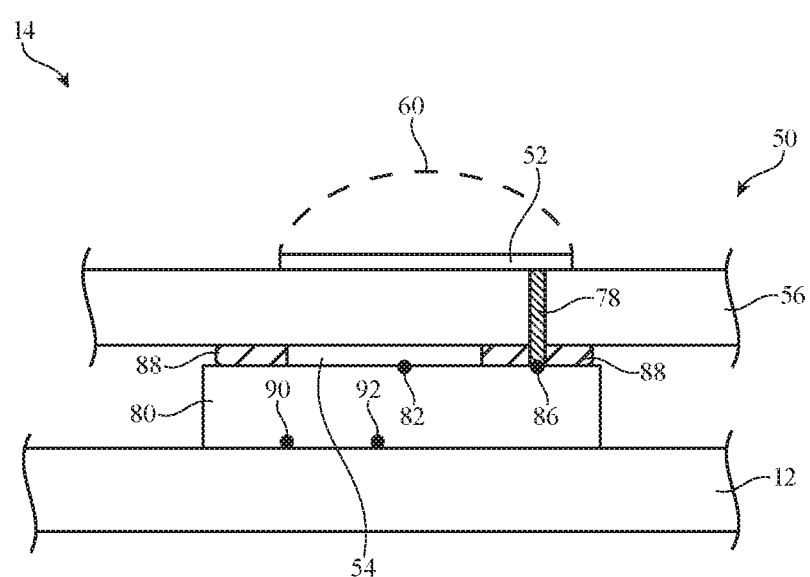
FIG. 16 is a cross-sectional side view of an illustrative force sensor formed from an integrated circuit that is coupled to signal lines such as conductive strands in a fabric layer and that is attached to an elastomeric layer with capacitive electrodes that are separated by the elastomeric layer in accordance with an embodiment.

FIG. 16 is a cross-sectional side view of an illustrative force sensor that includes an integrated circuit. As shown in FIG. 16, electrodes 52 and 54 of force sensing element 50 may be formed on opposing sides of substrate 56. Integrated circuit 80 may have terminals such as contacts 82 and 86. Contact 82 may be shorted to electrode 54. Via 78 may be formed from a conductor such as metal to short electrode 52 to contact 86. If desired, adhesive 88 (e.g., a polymer layer) may be used to attach integrated circuit 80 to substrate 56. Integrated circuit 80 may be a bare integrated circuit die (e.g., a silicon die) or may be a packaged integrated circuit (e.g., an integrated circuit die or dies mounted in package formed of plastic, ceramic, and/or other materials).

Integrated circuit 80 may include capacitive force sensor circuitry 48 of FIG. 6 and may analyze capacitive electrode measurements made using electrodes 54 and 52 to produce force sensor readings for use by control circuitry 16. Optional stiffener structures such as a structure 60 may be placed on electrode 52. Integrated circuit 80 may serve as a stiffener for electrode 54. Integrated circuit 80 may be coupled to control circuits in item 10 (e.g., control circuitry 16 of FIG. 4) using conductive paths such as conductive strands in fabric 12 or other conductive paths in item 10. Conductive strands of fabric 12 may be electrically coupled to integrated circuit terminals such as contacts 90 and 92 using solder, conductive adhesive, or other conductive material.

The signal paths in fabric 12 or other signal paths in item 10 that couple each integrated circuit 80 to control circuitry 16 may be used in conveying force measurements from force sensor elements 50 to control circuitry 16. One or more force sensor elements 50 may be coupled to each integrated circuit 80 to form force sensor circuitry for item 10. For example, there may be only a single element 50 coupled to each integrated circuit 80 or multiple elements 50 may be coupled to a given integrated circuit 80. Fabric 12 may be formed above and/or below force sensor components such as integrated circuit 80 and force sensor element(s) 50. For example, force sensor 14 may be embedded within fabric 12.

Figure 17:
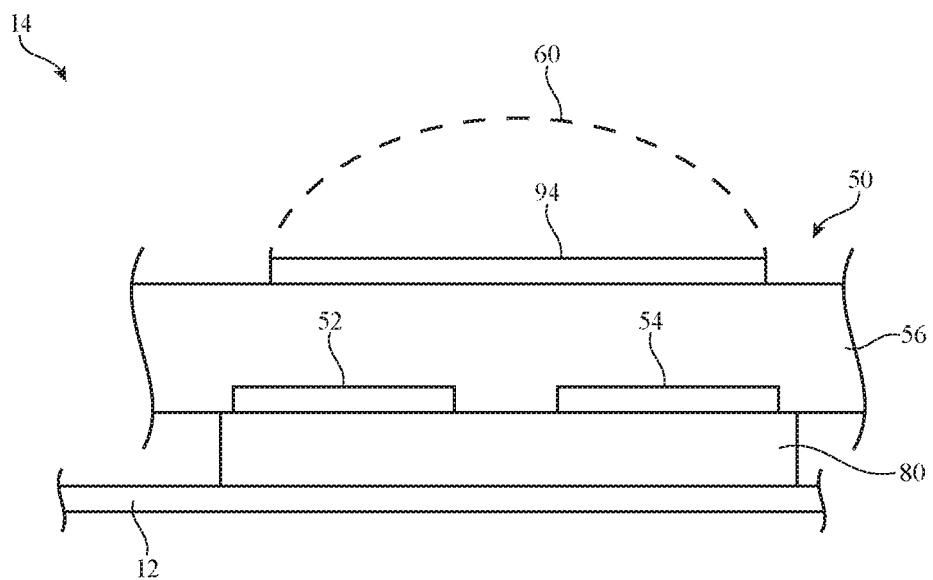
FIG. 17 is a cross-sectional side view of another illustrative force sensor formed from an integrated circuit and capacitive electrodes separated by an elastomeric layer that is attached to the integrated circuit in accordance with an embodiment.

In the illustrative configuration of FIG. 17, electrodes 52 and 54 have been placed on integrated circuit 80. Force sensor electrode 94 may be capacitively coupled to electrode 52 through substrate 56 and may be capacitively coupled to electrode 54 through substrate 56. Optional stiffener 60 may be formed on electrode 94. When the substrate material between electrode 94 and electrodes 52 and 54 is compressed by an applied force, the capacitive force sensor circuitry in integrated circuit 80 can detect the resulting capacitance change between electrode 52 and electrode 54 to measure the applied force.

Figure 18:
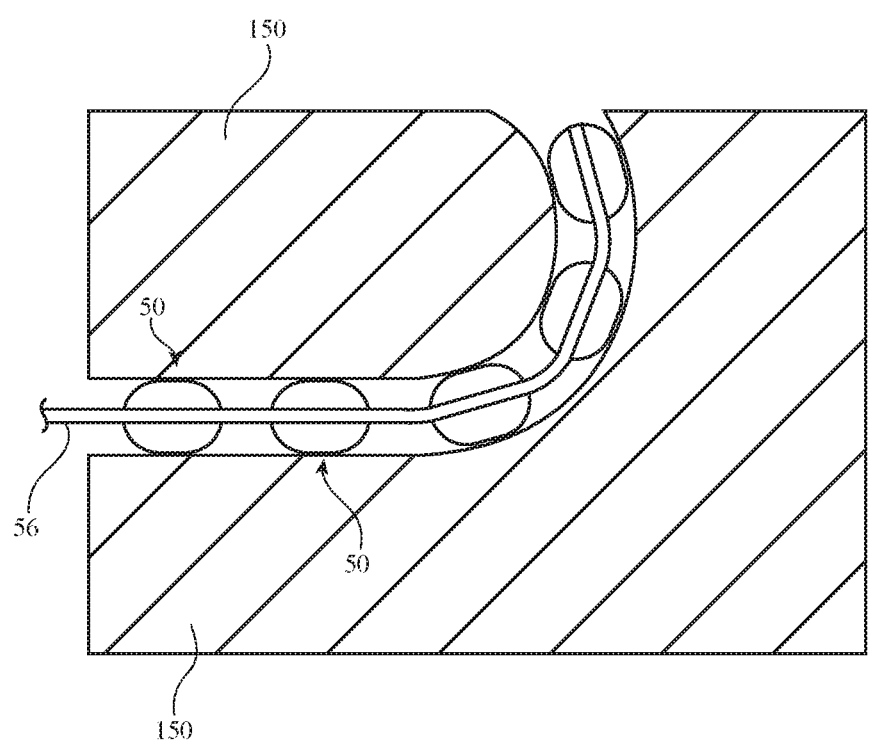
FIG. 18 is a cross-sectional side view of an illustrative force sensor being molded into a finger shape in accordance with an embodiment.

FIG. 18 shows how sensor 50 may be molded into the shape of a finger. After forming sensor elements 50 on substrate 56, heat and pressure may be applied to substrate 56 using finger-shaped molds 150. After molds 150 are removed, substrate 56 retains its molded shape, thereby producing force sensor circuitry in which substrate 56 and the array of elements on substrate 56 have compound curvature configured to receive a finger of a user. If desired, circuitry such as sensor elements 50 may be formed after substrate 56 has been molded into its desired shape (e.g., a finger shape having surfaces with compound curvature).

Figure 19:
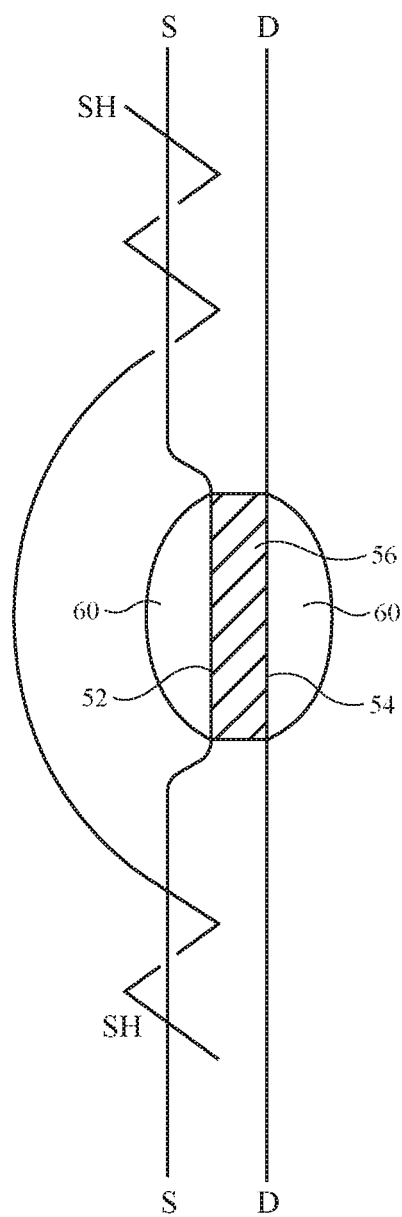
FIG. 19 is a cross-sectional side view of an illustrative yarn-based force sensor in accordance with an embodiment.

FIG. 19 shows how force sensor circuitry may be integrated into a yarn. Shield SH, sense line S, and drive line D may be formed from conductive strands of material. Portions of sense line S and drive line D and/or conductive traces on elastomeric substrate 56 (covered with optional stiffeners 60) may be used in forming electrodes for force sensing element 50. Shield SH may be braided with sense line S and drive line D. With one illustrative configuration, shield line SH may be twisted around sense line S to shield sense line S from interference with drive line D and drive line D may be loosely wrapped around both sense line S and shield line SH. In this way, a braided yarn with integral force sensing elements 50 along its length may be formed.

The foregoing is merely illustrative and various modifications can be made to the described embodiments. The foregoing embodiments may be implemented individually or in any combination.

What is claimed is:

1. Apparatus, comprising:
   fabric containing conductive strands of material that form signal paths;
   control circuitry coupled to the signal paths; and
   a force sensor coupled to the control circuitry, wherein the force sensor has a force sensor element and capacitive force sensor circuitry that is electrically coupled to the force sensor element through the signal paths and wherein the force sensor element includes a compressible substrate and first and second electrodes that are respectively located on first and second opposing surfaces of the compressible substrate.

2. The apparatus defined in claim 1 wherein the compressible substrate is an elastomeric polymer layer and wherein the force sensor element further comprises first and second stiffeners respectively on the first and second electrodes.

3. The apparatus defined in claim 2 wherein the elastomeric polymer layer is characterized by a first modulus of elasticity and wherein the stiffeners are characterized by a second modulus of elasticity that is greater than the first modulus of elasticity.

4. The apparatus defined in claim 3 wherein the compressible substrate has an elongated shape and forms a strand of material in the fabric.

5. The apparatus defined in claim 4 wherein the force sensor element comprises one of multiple force sensor elements in an array of force sensor elements on the compressible substrate.

6. The apparatus defined in claim 5 wherein the array is a one-dimensional array formed from a row of the force sensor elements.

7. The apparatus defined in claim 1 wherein the force sensor element comprises metal shielding layers on the compressible substrate.

8. The apparatus defined in claim 1 wherein the force sensor comprises a metal layer on the compressible substrate having serpentine signal lines.

9. A fabric force-sensing glove, comprising:
    glove fingers formed from fabric that has intertwined strands;
    control circuitry; and
    a force sensor coupled to the control circuitry, wherein the force sensor is formed from force sensor elements on an elongated strip-shaped polymer substrate that forms one of the intertwined strands.

10. The fabric force-sensing glove defined in claim 9 wherein the strip-shaped polymer substrate is formed from an elastomeric polymer and wherein the force senor elements extend in a row along the strip-shaped polymer substrate.

11. The fabric force-sensing glove defined in claim 10 wherein each force sensor element includes first and second electrodes and wherein each force sensor element includes a stiffener on the first electrode of that force sensor element.

12. The fabric force-sensing glove defined in claim 11 wherein there are openings in the polymer substrate surrounding the first electrode of each force sensor element.

13. The fabric force-sensing glove defined in claim 12 wherein the control circuitry includes wireless communications circuitry and wherein the control circuitry is configured to gather force sensor measurements from the force sensor and to wirelessly transmit the force sensor measurements with the wireless communications circuitry.

14. The fabric force-sensing glove defined in claim 9 wherein each force sensor element has electrodes on opposing surfaces of the strip-shaped polymer substrate.

15. The fabric force-sensing glove defined in claim 14 wherein each force sensor element has stiffeners on the electrodes.

16. The fabric force-sensing glove defined in claim 15 wherein the polymer substrate is characterized by a first elastic modulus and wherein the stiffeners are characterized by a second elastic modulus that is greater than the first elastic modulus.

17. A fabric-based item, comprising:
    fabric formed from intertwined strands of material including conductive strands; and
    force sensor circuitry in the fabric that is coupled to the conductive strands, wherein the force sensor circuitry includes integrated circuits containing capacitive force sensor circuitry and includes respective force sensor elements electrically coupled to the integrated circuits, wherein each force sensor element has capacitive force sensor electrodes on an elastomeric substrate that is attached to the integrated circuit.

18. The fabric-based item defined in claim 17 wherein the intertwined strands of material are configured to form glove fingers and wherein the force sensor elements are located on the glove fingers.

19. The fabric-based item defined in claim 18 wherein each force sensor element has a via that passes through the elastomeric substrate of that force sensor element and that shorts one of the capacitive force sensor electrodes of that force sensor element to the integrated circuit that is attached to that elastomeric substrate.

20. The fabric-based item defined in claim 19 wherein the conductive strands include first strands and second strands that cross the first strands at intersections and wherein the integrated circuits are coupled to the conductive strands at the intersections.

21. A fabric-based item, comprising:
    fabric formed from intertwined strands of material;
    control circuitry; and
    a force sensor coupled to the fabric and electrically coupled to the control circuitry, wherein the force sensor has a force sensor element and capacitive force sensor circuitry and wherein the force sensor element includes an elastomeric material, first and second electrodes separated by the elastomeric material, an electrical shield on the elastomeric material, and conductive traces on the elastomeric material that couple the first and second electrodes to the capacitive force sensor circuitry.

22. The fabric-based item defined in claim 21 wherein the electrical shield on the elastomeric material is electrically isolated from the first and second electrodes.

23. The fabric-based item defined in claim 21 wherein the conductive traces include sense and drive lines and wherein the electrical shield overlaps and electrically shields the sense line.

24. The fabric-based item defined in claim 23 wherein the elastomeric material forms a substrate having first and second elastomeric layers, wherein the first electrode is a sense electrode between the first and second elastomeric layers and wherein the second electrode is a drive electrode on the first elastomeric layer and separated from the first electrode by the first elastomeric layer.

25. The fabric-based item defined in claim 24 wherein the electrical shield includes a metal trace separated from the first electrode by the first elastomeric layer.

26. The fabric-based item defined in claim 25 wherein the electrical shield includes an additional metal trace separated from the first electrode by the second elastomeric layer.

27. The fabric-based item defined in claim 21 further comprising additional force sensor elements coupled to the capacitive force sensor circuitry with additional conductive traces on the elastomeric material.

28. The fabric-based item defined in claim 21 further comprising a stiffener on the first electrode.

29. The fabric-based item defined in claim 28 further comprising an additional stiffener on the second electrode.

\* \* \* \* \*

UNITED STATES PATENT AND TRADEMARK OFFICE
CERTIFICATE OF CORRECTION

PATENT NO. : 10,180,721 B2
APPLICATION NO. : 15/940876
DATED : January 15, 2019
INVENTOR(S) : Storrs T. Hoen et al.

It is certified that error appears in the above-identified patent and that said Letters Patent is hereby corrected as shown below:

In the Claims

Column 11, Line 41, Claim 10 "the force senor elements" should read -- the force sensor elements --

Signed and Sealed this
Eleventh Day of February, 2020

Andrei Iancu
*Director of the United States Patent and Trademark Office*